United States Patent [19]

Rizkalla

[11] Patent Number: 4,537,871
[45] Date of Patent: Aug. 27, 1985

[54] CARBONYLATION CATALYST

[75] Inventor: Nabil Rizkalla, River Vale, N.J.

[73] Assignee: The Halcon SD Group, Inc., New York, N.Y.

[21] Appl. No.: 602,648

[22] Filed: Apr. 23, 1984

Related U.S. Application Data

[62] Division of Ser. No. 429,925, Sep. 30, 1982, Pat. No. 4,483,803.

[51] Int. Cl.$^3$ ............... B01J 27/08; B01J 27/06; B01J 31/20; C07C 51/14
[52] U.S. Cl. ................. 502/161; 502/169; 502/170; 502/174; 502/224; 502/228; 502/229
[58] Field of Search ............... 502/161, 162, 169, 170, 502/174, 228, 229, 224

[56] References Cited

U.S. PATENT DOCUMENTS

| | | | |
|---|---|---|---|
| 3,821,265 | 6/1974 | Forster | 502/169 |
| 4,218,340 | 8/1980 | Holmes | 502/162 |
| 4,407,726 | 10/1983 | Rizkalla | 502/161 |
| 4,483,803 | 11/1984 | Rizkalla | 260/546 |
| 4,483,804 | 11/1984 | Rizkalla | 260/546 |

*Primary Examiner*—P. E. Konopka
*Attorney, Agent, or Firm*—William C. Long; Riggs T. Stewart; Harold N. Wells

[57] ABSTRACT

A liquid-phase catalyst is represented by the formula X:T:Z:Q, wherein X is molybdenum, tungsten or chromium, T is nickel, X and T being in zero valent form or in the form of a halide, an oxide, a carboxylate of 1 to 20 carbon atoms, a carbonyl or an hydride; Z is a halide source which is hydrogen halide, halogen, or an alkyl halide wherein the alkyl group contains 1 to 20 carbon atoms, and Q is the alkali metal component and is in the form of an iodide, a bromide, a chloride or a carboxylate as defined for X and T, the molar ratio of X to T being 0.1–10:1, the molar ratio of X+T to Q being 0.1–10:1, and the molar ratio of Z to X+T being 0.01–0.1:1.

1 Claim, No Drawings

CARBONYLATION CATALYST

This is a division of application Ser. No. 429,925 filed Sept. 30, 1982, now U.S. Pat. No. 4,483,803.

This invention relates to the preparation of anhydrides of carboxylic acids, more particularly mono-carboxylic acids and especially the anhydrides of lower alkanoic acids, such as propionic anhydride, by the carbonylation of olefins.

The production of anhydrides by the action of carbon monoxide upon olefins (carbonylation) has been described, for example, in Reppe et al U.S. Pat. No. 2,768,968. However, this proposal requires the use of very high pressures. In later patents, carbonylation of olefins at lower pressures has been proposed. Foster et al U.S. Pat. No. 3,852,346 describes the carbonylation of olefins in the presence of compounds of Group VIII noble metals such as iridium and rhodium and in the presence of an iodide under more moderate pressures than those contemplated by Reppe et al. However, this process suffers from the need to employ expensive, relatively rare metals.

In my U.S. Pat. No. 4,335,058 dated June 15, 1982, and entitled "Preparation of Carboxylic Acid Anhydrides," there is disclosed a related process for the carbonylation of olefins to produce carboxylic acid anhydrides which uses a molybdenum-nickel or tungsten-nickel co-catalyst in the presence of a promoter comprising an organo-phosphorus or an organo-nitrogen compound, such as a phosphine or a tertiary amine. While this process involves nickel catalysts which make possible carbonylation of olefins at modest pressures without requiring the use of a noble metal catalyst, and while this process is highly effective for its intended purpose, there is room for improvement in terms of reaction rate and productivity without need to use organic promoters.

It is accordingly an object of the present invention to provide an improved process for the manufacture of anhydrides of carboxylic acids, especially anhydrides of lower alkanoic acids, such as propionic anhydride, by the carbonylation of the appropriate olefin, which requires neither high pressures nor Group VIII noble metal catalysts and at the same time makes possible the production of such anhydrides in high yields in short reaction times without need to use organic promoters.

In accordance with the invention, carbonylation of an olefin is carried out by using a molybdenum-nickel-alkali metal, a tungsten-nickel-alkali metal or a chromium-nickel-alkali metal co-catalyst in the presence of a halide, preferably an iodide, a bromide, and/or a chloride, especially an iodide, and in the presence of a carboxylic acid. The surprising discovery has been made that this co-catalyst system, in an environment of the character indicated, makes possible the carbonylation of olefins not only at relatively low pressures but with rapid, high yield production of carboxylic acid anhydrides.

The outstanding effectiveness of the catalyst system of the process of this invention is particularly surprising in view of the experimental data reported in European published application No. 0 035 458 which shows the carbonylation of methanol to produce acetic acid and in which experiments using nickel in combination with molybdenum or tungsten or chromium showed absolutely no reaction even after two hours. It has also been observed that when nickel-based catalysts are ordinarily used in carbonylation reactions, there is a tendency for the nickel components to be volatilized and to appear in the vapors from the reaction. It has been surprisingly found that, with the catalyst system of this invention, the volatility of the nickel is strongly suppressed and a highly-stable catalyst combination results, especially in the case of the molybdenum-containing co-catalyst, which is the preferred co-catalyst.

Thus, in accordance with the invention, carbon monoxide is reacted with an olefin, especially a lower alkene, to produce a carboxylic anhydride, such as a lower alkanoic anhydride, the carbonylation taking place in the presence of a halide, e.g., a hydrocarbyl halide, especially a lower alkyl halide, such as ethyl iodide, and a carboxylic acid. Thus, propionic anhydride, for example, can be effectively prepared in a representative case by subjecting ethylene to carbonylation in the presence of ethyl iodide and in the presence of propionic acid. In all cases, the carbonylation is carried out under anhydrous conditions in the presence of the co-catalyst system described above.

It will be understood that the halide moiety does not have to be added to the system as a hydrocarbyl halide but may be supplied as another organic halide or as the hydrohalide or other inorganic halide, e.g, a salt, such as the alkali metal or other metal salt, or even as the elemental halide, e.g., elemental iodine. Following the reaction, the organic components of the reaction mixture are readily separated from one another, as by fractional distillation.

In like manner, other lower alkanoic anhydrides, i.e., anhydrides of lower alkanoic acids, such as i-butyric anhydride, n-butyric anhydride, and valeric anhydride, can be produced by carbonylating the corresponding lower alkene. Similarly, other carboxylic acid anhydrides, e.g., the anhydrides of other alkanoic acids, for example, capric anhydrides, caprylic anhydrides and lauric anhydrides, and like higher anhydrides are produced by carbonylating the corresponding olefin.

The reactant olefin may be any ethylenically unsaturated hydrocarbon having from 2 to about 25 carbon atoms, preferably from 2 to about 15 carbon atoms. The ethylenically unsaturated compound has the following general structure:

$$R_2R_1C\!=\!CR_3R_4$$

wherein $R_1$, $R_2$, $R_3$ and $R_4$ are hydrogen or the same or different alkyl, cycloalkyl, aryl, alkaryl, aralkyl or wherein one of said $R_1$ and $R_2$ and one of said $R_3$ and $R_4$ together form a single alkylene group having from 2 to about 8 carbon atoms. $R_1$, $R_2$, $R_3$ and $R_4$ can be branched and can be substituted with substituents which are inert in the reactions of the invention.

Examples of useful ethylenically unsaturated hydrocarbons are ethylene, propylene, butene-1, butene-2, 2-methylbutene-1, cyclobutene, hexene-1, hexene-2, cyclohexene, 3-ethylhexene-1, isobutylene, octene-1,2-methylhexene-1, ethylcyclohexene, decene-1, cycloheptene, cyclooctene, cyclononene, 3,3-dimethylnonene-1, dodecene-1, undecene-3, 6-propyldecene-1, tetradecene-2, 3-amyldecene-1, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, divinylbenzene, 1-allyl-3-vinylbenzene, etc. Of the olefins referred to above, the alpha hydrocarbon olefins and olefins having 2 to about 10 carbon atoms are preferred, e.g., ethylene, propylene, butene-1, hexene-1, heptene-1, octene-1, and the like, i.e. wherein $R_1$, $R_2$, $R_3$ and $R_4$ are hydrogen or alkyl groups totalling 1–8 carbon atoms, preferably the lower alkenes, i.e. alkenes of 2 to 6 carbon atoms, especially ethylene.

The reactant carboxylic acid may be in general any carboxylic acid having 1 to about 25 carbons and having the formula:

RCOOH wherein R is hydrogen, alkyl, cycloalkyl or aryl. Preferably R has 1 to about 18 carbon atoms and most preferably R is alkyl having 1 to about 12 carbon atoms, especially 1 to 6 carbon atoms e.g., methyl, ethyl, propyl, isobutyl, hexyl, nonyl, and the like, or is aryl with 6 to about 9 carbon atoms, e.g., phenyl, tolyl, and the like.

Examples of useful acids are acetic, propionic, n-butyric, isobutyric, pivalic, n-valeric, n-caproic, caprylic, capric, decanoic, myristic, palmitic, naphthoic, stearic, benzoic, phthalic terephthalic, toluic, 3-phenylhexanoic acid, 2-xylylpalmitic acid and 4-phenyl-5-isobutyl stearic acid. The preferred acids are the fatty or alkanoic acids having 2 to about 12 carbon atoms, e.g., acetic, propionic, n-butyric, isobutyric, pivalic, caproic, undecylic, and the like. Especially preferred are the lower alkanoic acids i.e. wherein R is an alkyl group of 1 to 6 carbon atoms, especially propionic acid. R can be branched and can be substituted with substituents which are inert in the reactions of the invention.

It is preferred that the reactants be selected so that the resulting anhydride will be a symmetrical anhydride, i.e., having two identical acyl groups.

In the most preferred embodiment of the invention carbon monoxide is reacted with ethylene and propionic acid in the presence of the co-catalyst halide system of the character described above to produce propionic anhydride in a reaction which may be expressed as follows:

$$C_2H_4+CO+C_2H_5COOH \rightarrow C_2H_5COOCOC_2H_5$$

Carbon monoxide is removed in the vapor phase along with unreacted olefin when the olefin is normally gaseous, e.g., ethylene and, if desired, recycled. Normally liquid and relatively volatile components such as alkyl halide and unreacted normally-liquid olefin and carboxylic acid and by-products present in the final product mixture can be readily removed and separated from each other, as by distillation, for recycling, and the net yield of product is substantially exclusively the desired carboxylic anhydride. In the case of liquid-phase reaction, which is preferred, the organic compounds are easily separated from the metal-containing components, as by distillation, The reaction is suitably carried out in a reaction zone to which the carbon monoxide, the olefin, the acid, the halide, the specified co-catalyst combination are fed. No water is produced in the above-described reactions and anhydrous conditions are employed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 2,000 psi and most preferably 30 to 1,200 psi, although carbon monoxide partial pressures of 1 to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time, the reaction mixture is separated into several constituents, as by distillation. Preferably, the reaction product is introduced into a distillation zone which may be a fractional distillation column, or a series of columns, effective to separate the volatile components from the product anhydride catalyst and promoter components of the reaction mixture. The boiling points of the volatile components are sufficiently far apart that their separation by conventional distillation presents no particular problem. Likewise, the higher boiling organic components can be readily distilled away from the metal co-catalyst components. The co-catalyst components can then be combined with fresh amounts of olefin, carboxylic acid and carbon monoxide and reacted to produce additional quantities of anhydride.

Although not necessary, the process can be carried out in the presence of a solvent or diluent. The presence of a higher boiling solvent or diluent, which may be the product anhydride itself, e.g., propionic anhydride in the case of ethylene, will make it possible to employ more moderate total pressure. Alternatively, the solvent or diluent may be any organic solvent which is inert in the environment of the process, such as hydrocarbons, e.g., octane, benzene, toluene, or carboxylic acids, e.g., propionic acid, and the like. Excess carboxylic acid, when used as a solvent, should correspond to the carboxylic acid being reacted. A solvent or diluent, when not the product itself, is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present, if desired. The presence of inert diluents does not affect the carbonylation reaction, but their presence makes it necessary to increase the total pressure in order to maintain the desired CO partial pressure. Hydrogen which may be present as an impurity is not objectionable and even may tend to stabilize the catalyst. Indeed, in order to obtain low CO partial pressures, the CO fed may be diluted with hydrogen or any inert gas such as those mentioned above. The diluent gas, e.g., hydrogen, may generally be used in an amount up to about 95%, if desired.

The co-catalyst components can be employed in any convenient form, viz., in the zero valent state or in any higher valent form. For example, the nickel and the molybdenum, tungsten or chromium can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or Mo, W, Cr or Ni carboxylates wherein the carboxylate ion is derived from an alkanoic acid of 1 to 20 carbon atoms, such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl.

Particularly preferred are the elemental forms, compounds which are halides, especially iodides, and organic salts, e.g., salts of the monocarboxylic acid corresponding to the acid being produced.

The alkali metal component, e.g., a metal of Group IA of the Periodic Table such as lithium, potassium, sodium, and cesium, is suitably employed as a compound, especially a salt, and most preferably a halide, e.g., an iodide. The preferred alkali metal is lithium. The alkali metal component can, however, also be employed as the hydroxide, carboxylate, alkoxide or in the form of other convenient compounds such as are referred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

It will be understood that the above-mentioned compounds and complexes are merely illustrative of suitable forms of the several co-catalyst components and are not intended to be limiting.

The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter of reaction mixture, preferably 15 millimoles to 500 millimoles per liter and most preferably 15 millimoles to 150 millimoles per liter.

The ratio of nickel to the molybdenum, tungsten, or chromium co-catalyst component can vary. Typically, it is one mol of the nickel component per 0.01 to 100 mols of the second co-catalyst component, i.e., the molybdenum, tungsten, or chromium component, preferably the nickel component is used in the amount of 1 mol per 0.1 to 20 mols, most preferably 1 mol per 1 to 10 mols of the second co-catalyst component. Similarly, the ratio of nickel to the alkali metal component can vary, e.g. one mol of nickel per 1 to 1000 mols of alkali metal component, preferably 10 to 100 and most preferably 20 to 50.

The amount of halide component may also vary widely but, in general, it should be present in an amount of at least 0.1 mol (expressed as elemental halogen) per mol of nickel. Typically, there are used 1 to 100 mols of the halide per mol of nickel, preferably 2 to 50 mols per mol. Ordinarily, more than 200 mols of halide per mol of nickel are not used. It will be understood, however, that the halide component does not have to be added to the system as a hydrocarbyl halide but may be supplied as another organic halide or as the hydrohalide or other inorganic halide, e.g., a salt, such as the alkali metal or other metal salt, or even as elemental halogen, e.g., iodine or bromine.

As previously mentioned, the catalyst system of this invention comprises a halide, especially an iodide, component and a molybdenum-nickel-alkali metal, tungsten-nickel-alkali metal, or chromium-nickel-alkali metal co-catalyst component. The catalyst system of this invention permits the production of carboxylic anhydrides in high yields in short reaction times without the use of Group VIII noble metals, and the presence of the alkali metal component together with the molybdenum, tungsten or chromium component makes possible good results with relatively small amounts of co-catalyst components and reduced quantities of nickel in comparison with prior art processes involving a nickel-containing catalyst.

A particular embodiment of the catalyst comprising the molybdenum-nickel-alkali metal, tungsten-nickel-alkali metal, or chromium-nickel-alkali metal co-catalyst component and the halide component can be represented by the following formula: Z:T:Z:Q, wherein X is molybdenum, tungsten or chromium, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is the alkali metal component. The preferred alkali metal is lithium as previously indicated, and is in the form of an iodide, a bromide, a chloride or a carboxylate as defined for X and T, the molar ratio of X to T being 0.1–10:1, the molar ratio of X+T to Q being 0.1–10:1, and the molar ratio of Z to X+T being 0.01–0.1:1.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight, unless otherwise indicated.

EXAMPLE 1

A magnetically-stirred pressure vessel with a glass liner was charged with 68 parts propionic acid, 12 parts iodoethane, 0.8 part nickel iodide, 1.6 parts molybdenum hexacarbonyl, and 16 parts lithium iodide. The vessel was swept out with argon and was pressured to 100 p.s.i.g. with hydrogen and then up to 500 p.s.i.g. with carbon monoxide. The vessel was heated to 160° C. with stirring and the pressure was brought up to 800 p.s.i.g. with ethylene. The pressure was maintained at 800 p.s.i.g. by recharging a 1:1 mixture of ethylene and carbon monoxide and the temperature was maintained at 160° C. After 50 minutes reaction, G.C. analysis of the reaction mixture showed propionic anhydride had been formed at the rate of 10 mols per liter per hour and that all of the ethylene reacted had been converted to propionic anhydride.

EXAMPLE 2

A magnetically-stirred pressure vessel with a glass liner was charged with 68 parts propionic acid, 1.6 parts molybdenum hexacarbonyl, 0.8 part nickel iodide, 12 parts ethyl iodide and 16 parts lithium iodide. The vessel was swept out with argon and was pressured to 100 p.s.i.g. with hydrogen and then up to 500 p.s.i.g. with carbon monoxide. The vessel was heated to 180° C. with stirring. The pressure was brought up to 750 p.s.i.g. with ethylene and the pressure was maintained at 750 p.s.i.g. by recharging a 1:1 mixture of ethylene and carbon monoxide. The temperature was maintained at 180° C. After 1 hour of reaction, G.C. analysis of the reaction mixture showed that propionic anhydride had been formed at the rate of 7.1 mols per liter per hour and that all of the ethylene reacted had been converted to propionic anhydride.

EXAMPLE 3

Example 1 was repeated with the exception that temperature maintained at 140° C. and reacting was for 1 hour. G.C. analysis of the reaction mixture showed propionic anhydride had been formed at the rate of 3.2 mols per liter per hour and that all of the ethylene reacted had been converted to propionic anhydride.

EXAMPLE 4

Example 2 was repeated with the exception that molybdenum hexacarbonyl was replaced with an equal amount of tungsten hexacarbonyl. After 1 hour of reaction, G.C. analysis of the reaction mixture showed that propionic anhydride had been formed at rate of 1.8 mols per liter per hour and that all of the ethylene reacted had been converted to propionic anhydride.

EXAMPLE 5

Example 2 was repeated with the exception that lithium iodide was replaced with an equal amount of potassium iodide. After 2 hours of reaction, G.C. analysis showed that propionic anhydride had been formed at the rate of 0.7 mols per liter per hour and that all of the ethylene reacted had been converted to propionic anhydride.

EXAMPLE 6

Example 2 was repeated with the exception that lithium iodide was replaced with equal amount of cesium iodide. After 1 hour of reaction, G.C. analysis showed propionic anhydride formed at rate of 1.9 mols per liter per hour and that all of the ethylene reacted had been converted to propionic anhydride.

EXAMPLE 7

Example 2 was repeated except that no hydrogen was charged after 1 hour of reaction. G.C. analysis of the reaction effluent showed that propionic anhydride had been formed at the rate of 2.3 mols per liter per hour and that all of the ethylene reacted had been converted to propionic anhydride.

COMPARATIVE EXAMPLE A

Example 2 was repeated with the exception that no lithium iodide was charged. After one hour of reaction, G.C. analysis showed that propionic anhydride had been formed at rate of only 0.2 mol per liter per hour.

COMPARATIVE EXAMPLE B

Example 2 was repeated with the exception that no molybdenum hexacarbonyl was charged. After 1 hour of reaction, G.C. analysis showed that propionic anhydride formed at rate of 0.5 mol per liter per hour.

What is claimed is:

1. A liquid-phase carbonylation catalyst consisting essentially of a molybdenum-nickel-alkali metal, tungsten-nickel-alkali metal, or chromium-nickel-alkali metal co-catalyst component and a halide component represented by the following formula: X:T:Z:Q, wherein X is molybdenum, tungsten or chromium, T is nickel, X and T being in zero valent form or in the form of a halide, an oxide, a carboxylate of 1 to 20 carbon atoms, a carbonyl or an hydride; Z is a halide source which is hydrogen halide, halogen, or an alkyl halide wherein the alkyl group contains 1 to 20 carbon atoms, and Q is the alkali metal component and is in the form of an iodide, a bromide, a chloride or a carboxylate as defined for X and T, the molar ratio of X to T being 0.1–10:1, the molar ratio of X+T to Q being 0.1–10:1, and the molar ratio of Z to X+T being 0.01–0.1:1.

* * * * *